US009408920B2

(12) United States Patent
Chung et al.

(10) Patent No.: US 9,408,920 B2
(45) Date of Patent: Aug. 9, 2016

(54) CELL-PENETRATING FUSION PROTEIN FOR REGENERATING OR PROLIFERATING STEM CELL

(75) Inventors: Chong-Pyoung Chung, Seoul (KR); Yoon-Jeong Park, Seoul (KR); Jue-Yeon Lee, Gyeonggi-do (KR)

(73) Assignees: SEOUL NATIONAL UNIVERSITY R AND DB FOUNDATION, Seoul (KR); NANO INTELLIGENT BIOMEDICAL ENGINEERING CORPORATION CO, LTD., Seoul (KR)

( * ) Notice: Subject to any disclaimer, the term of this patent is extended or adjusted under 35 U.S.C. 154(b) by 0 days.

(21) Appl. No.: 14/119,160

(22) PCT Filed: Dec. 16, 2011

(86) PCT No.: PCT/KR2011/009709
§ 371 (c)(1),
(2), (4) Date: Nov. 20, 2013

(87) PCT Pub. No.: WO2012/165737
PCT Pub. Date: Dec. 6, 2012

(65) Prior Publication Data
US 2014/0377243 A1    Dec. 25, 2014

(30) Foreign Application Priority Data
May 30, 2011   (KR) .................. 10-2011-0051621

(51) Int. Cl.
*A61K 38/00* (2006.01)
*C07K 16/00* (2006.01)
*A61K 47/48* (2006.01)
*C07K 14/51* (2006.01)
*C12N 9/02* (2006.01)
*C07K 14/47* (2006.01)

(52) U.S. Cl.
CPC ....... *A61K 47/48246* (2013.01); *C07K 14/4702* (2013.01); *C07K 14/51* (2013.01); *C12N 9/0036* (2013.01); *C12N 9/0089* (2013.01); *C07K 2319/10* (2013.01); *C07K 2319/21* (2013.01); *C07K 2319/35* (2013.01); *C07K 2319/73* (2013.01)

(58) Field of Classification Search
None
See application file for complete search history.

(56) References Cited

U.S. PATENT DOCUMENTS

2003/0167524 A1 * 9/2003 Rooijen et al. ............ 800/281

FOREIGN PATENT DOCUMENTS

KR    10-0568457 B1    3/2006
WO    2005007860 A1    1/2005

OTHER PUBLICATIONS

Kwon et. al., FEBS Letters 485 (2000) 163-167.*
Song, Stem Cells and Development. vol. 20, No. 9, 2011.*
Kwon, FEBS letters, 485 (2000) 163-167.*
Domashenko et. al. Blood. Oct. 14, 2010; 116(15): 2676-2683.*
Borghouts et al. Mol Cancer Res 2008;6(2). Feb. 2008.*
Domashenko, A., et al., "TAT-mediated transduction of NF-Ya peptide induces the ex vivo proliferation and engraftment potential of human hematopoietic progenitor cells", "Blood", Oct. 14, 2010, pp. 2676-2683, vol. 116, No. 15.
Frankel, A., et al., "Cellular Uptake of the Tat Protein from Human Immunodeficiency Virus", "Cell", Dec. 23, 1988, pp. 1189-1193, vol. 55.
Gersbach, C., et al., "In Vitro and In Vivo Osteoblastic Differentiation of BMP-2- and Runx2-Engineered Skeletal Myoblasts", "Journal of Cellular Biochemistry", 2007, pp. 1324-1336, vol. 100.
Green, M., et al., "Autonomous Functional Domains of Chemically Synthesized Human Immunodeficiency Virus Tat Trans-Activator Protein", "Cell", Dec. 23, 1988, pp. 1179-1188, vol. 55.
Hong, J., et al., "TAZ, a Transcriptional Modulator of Mesenchymal Stem Cell Differentiation", "Science", Aug. 12, 2005, pp. 1074-1078, vol. 309.
Kwon, H., et al., "Transduction of Cu,Zn-superoxide dismutase mediated by an HIV-1 Tat protein basic domain into mammalian cells", "FEBS Letters", Nov. 7, 2000, pp. 163-167, vol. 485.
Ma, H. et al., "Molecular Determinants for Cellular Uptake of Tat Protein of Human Immunodeficiency Virus Type 1 in Brain Cells", "Journal of Virology", Mar. 1997, pp. 2495-2499, vol. 71, No. 3.
Song, J., et al., "Role of Thioredoxin 1 and Thioredoxin 2 on Proliferation of Human Adipose Tissue-Derived Mesenchymal Stem Cells", "Stem Cells and Development", Sep. 2011, pp. 1529-1537, vol. 20, No. 9.
Vives, E., et al., "A Truncated HIV-1 Tat Protein Basic Domain Rapidly Translocates through the Plasma Membrane and Accumulates in the Cell Nucleus", "The Journal of Biological Chemistry", Jun. 20, 1997, pp. 16010-16017, vol. 272, No. 25.
Zhang, D., et al., "A novel TAT fusion protein with osteoinductive activity", "Medical Hypotheses", 2007, pp. 1009-1011, vol. 68.
Note: For the non-patent literature citations that no month of publication is indicated, the year of publication is more than 1 year prior to the effective filing date of the present application.
Doeppner, T., et al., "Transplantation of TAT-Bcl-xL-transduced neural precursor cells: Long-term neuroprotection after stroke", "Nerurobiology of Disease", Jun. 8, 2010, pp. 265-276, vol. 40.
Domashenko, A., et al., "Transduction of Human CD34+ Cells With Recombinant TAT-NF-YA Protein Enhances Their Ex Vivo Expansion and Repopulating Potential in NOD/SCID Mice", "Blood (ASH Annual Meeting Abstracts)", 2008, Page(s) Abstract 3528, vol. 112.
Kim., W., et al., "PEP-1-Frataxin Significantly Increases Cell Proliferation and Neuroblast Differentiation by Reducing Lipid Peroxidation in the Mouse Dentate Gyrus", "Neurochem Res", Sep. 1, 2011, pp. 2452-2458, vol. 36.

(Continued)

Primary Examiner — Jeanette Lieb
(74) Attorney, Agent, or Firm — Hultquist, PLLC; Steven J. Hultquist

(57) ABSTRACT

The present invention relates to a cell permeable fusion protein for strengthening regenerative potential of stem cells, and more particularly to a cell permeable fusion protein for strengthening regenerative potential of stem cells for stimulating the differentiation of stem cells, inhibiting apoptosis, maintaining the functionality of stem cells and restoring the stress-inhibited functionality of stem cells.

11 Claims, 5 Drawing Sheets

(56) References Cited

OTHER PUBLICATIONS

Sanvageau, G., "Manipulating Stem Cells for Therapeutic Expansion", "Blood (ASH Annual Meeting Abstracts)", 2009, Page(s) Abstract 42, vol. 114.

Society for Experimental Biology and Medicine USA, "Improvement of liver stem cell engraftment by protein delivery", "Experimental Biology and Medicine", Sep. 2009, Page(s) vi, vol. 234, No. 9.

* cited by examiner mouse C2C12

CELL-PENETRATING FUSION PROTEIN FOR REGENERATING OR PROLIFERATING STEM CELL

CROSS-REFERENCE TO RELATED APPLICATIONS

This application is a U.S. national phase under the provisions of 35 U.S.C. §371 of International Patent Application No. PCT/KR11/09709 filed Dec. 16, 2011, which in turn claims priority of Korean Patent Application No. 10-2011-0051621 filed May 30, 2011. The disclosures of such international patent application and Korean priority patent application are hereby incorporated herein by reference in their respective entireties, for all purposes.

TECHNICAL FIELD

The present invention relates to a cell permeable fusion protein for strengthening regenerative potential of stem cells, and more particularly to a cell permeable fusion protein for strengthening regenerative potential of stem cells for stimulating the differentiation of stem cells, inhibiting apoptosis, maintaining the functionality of stem cells and restoring the stress-inhibited functionality of stem cells.

BACKGROUND ART

The term "mesenchymal stem cells" refers to cells that are involved in the development and growth of the skeletal system in their embryonic stage and have the capability to differentiate into various kinds of skeletal cells, including osteocytes, chondrocytes, myocytes, fibrocytes, etc., after completion of growth. The mesenchymal stem cells are also referred to as bone marrow stromal stem cells. Unlike embryonic stem cells, mesenchymal stem cells do not cause tumors or ethical issues, and thus are highly useful for clinical applications.

However, the problems to be solved in the transplantation of stem cells are developing technology for facilitating engraftment (improving adaptability) and proliferation in vivo after transplantation and ensuring the capability to differentiate selectively into a desired tissue. To improve adaptability in vivo after transplantation, immune-related drugs are administered after transplantation. However, these drugs are administered to improve the adaptability of a subject to which stem cells are transplanted. A substance for improving the adaptability of the cells transplanted has not been reported yet.

The stem cells transplanted by the surrounding tissue environment undergo senescence, die out, and thus cannot exhibit effects of transplantation. In addition, smooth proliferation of the transplanted stem cells may be the first consideration for regeneration of the cells. In addition to engraftment and proliferation, a substance for stimulating selective differentiation into a desired tissue (bone tissue in the present invention) has also not been reported. Transcription factors essential in the differentiation of mesenchymal stem cells into osteoblasts and adipocytes are Runx2 and peroxisome proliferator-activated receptor-gamma (PPAR-gamma). These factors induce mesenchymal stem cells to differentiate into osteoblasts which produce bones and adipocytes. Runx2 is a protein which is observed to be localized to bone when injected externally, and in addition to this protein, several proteins are known to stimulate the differentiation of cells into bone tissue. Particularly, Hong et al. demonstrated that a 14-3-3-binding protein, TAZ (transcriptional coactivator with PDZ-binding motif), represses PPAR gamma transcription and activates Runx2 (Hong J. H. et al., *Science*, 309:1074, 2005). These proteins act to activate genes for osteogenic differentiation in the cytoplasm. However, the molecular weight of these proteins is too large to be introduced into the cytoplasm or tissue for a specific purpose (substances having a molecular weight of 600 or more are almost impossible to pass through the cell membrane). For this reason, the use of carriers to introduce these proteins into cells is acutely required.

Recently, the development of osteogenesis stimulators for repairing bone damaged by osteoporosis, bone fracture or surgery has been required. However, osteogenesis stimulators, such as bisphosphonates, calcitonin, estradiol or vitamin D, developed to date, mainly aim to inhibit bone resorption, and are not significantly effective to the regeneration of lost bone. Thus, many efforts have been made to discover new drugs that can stimulate osteogenesis.

In recent years, it was found that Tat (transactivator of transcription) protein, a kind of human immunodeficiency virus type-1, efficiently passes through the cell membrane and migrates into the cytoplasm. This function appears because of the characteristics of the protein transduction domain (PTD) of the Tat protein, and the exact mechanism thereof is not known yet (Frankel, A. D. and Pabo, C. O., *Cell*, 55:1189, 1988; Green, M. and Loewenstein, P. M., *Cell*, 55:1179, 1988; Ma, M. and Nath, A., *J. Virol.*, 71:2495, 1997; Vives, E. et al., B. *J. Biol. Chem.*, 272:16010, 1997).

Meanwhile, since it was found that a fusion protein obtained by linking PTD to other peptides or proteins is efficiently transported into cells, various applications using PTD has been attempted (Korean Patent Registration No. 10-0568457). However, there has not yet been an attempt to apply the transcription factor NF-Ya or antioxidant protein (e.g., SOD, thioredoxin, etc.) linked to a cell-penetrating peptide to tissue engineering for the purposes of promoting the engraftment of mesenchymal stem cells and inducing the proliferation thereof.

Accordingly, the present inventors have made extensive efforts to develop a cell permeable fusion protein for strengthening regenerative potential of stem cells, and as a result, have prepared a fusion protein by linking a cell-penetrating protein to the amino terminal of an antioxidant protein or a protein having the ability to improve cell proliferation, and have found that the fusion protein can increase the success rate of transplantation of stem cells, can be used to prevent and treat bone disease by selectively inducing the regeneration of bone tissue, can efficiently deliver a protein that inhibits adipocytes into cells, is easily synthesized, and causes no toxicity problem, thereby completing the present invention.

DISCLOSURE OF INVENTION

Technical Problem

It is an object of the present invention to provide a cell permeable fusion protein for strengthening regenerative potential of stem cells.

Technical Solution

To achieve the above object, the present invention provides a cell permeable fusion protein for strengthening regenerative potential of stem cells, wherein a cell permeable peptide is linked to the amino terminal of an antioxidant protein or a protein having an ability to improve cell proliferation.

The present invention also provides a cell permeable fusion protein for strengthening regenerative potential of stem cells, wherein a cell permeable peptide is linked to the amino terminal of the fusion protein of an antioxidant protein and a protein having the ability to improve cell proliferation.

The present invention also provides a vector for expressing a cell permeable fusion protein for strengthening regenerative potential of stem cells, the vector comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines.

The present invention also provides a recombinant microorganism transformed with a vector for expressing a cell permeable fusion protein for strengthening regenerative potential of stem cells, the vector comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines.

The present invention also provides a method for preparing a cell permeable fusion protein for strengthening regenerative potential of stem cells, the method comprising the steps of: culturing a recombinant microorganism transformed with a vector for expressing a cell permeable fusion protein for strengthening regenerative potential of stem cells, the vector comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines; and recovering the expressed fusion protein.

The present invention also provides a method for regeneration of stem cells, by the method for preparing a cell permeable fusion protein for strengthening regenerative potential of stem cells, the method comprising the steps of: culturing a recombinant microorganism transformed with a vector for expressing a cell permeable fusion protein for strengthening regenerative potential of stem cells, the vector comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines; and recovering the expressed fusion protein.

The present invention also provides a cell permeable fusion protein for promoting osteogenesis, wherein a cell permeable peptide is linked to the terminal of the fusion protein of a transcription factor protein for inducing osteogenic differentiation and an antioxidant protein or a protein having the ability to improve cell proliferation.

The present invention also provides a pharmaceutical composition for treating bone diseases, wherein the composition comprising a cell permeable fusion protein for promoting osteogenesis, wherein a cell permeable peptide is linked to the terminal of the fusion protein of a transcription factor protein for inducing osteogenic differentiation and an antioxidant protein or a protein having the ability to improve cell proliferation, as an active ingredient.

The present invention also provides a health functional food for treating bone diseases, wherein the food comprising a cell permeable fusion protein for promoting osteogenesis, wherein a cell permeable peptide is linked to the terminal of the fusion protein of a transcription factor protein for inducing osteogenic differentiation and an antioxidant protein or a protein having the ability to improve cell proliferation, as an active ingredient.

BRIEF DESCRIPTION OF THE DRAWINGS

FIG. 3A shows a cellular morphological change caused by treatment of a LMWP-SOD fusion protein, and FIGS. 3B and 3C show the results of staining with senescence associated beta-galactosidase.

FIGS. 4A and 4B show the results of RT-PCR of p53 gene and p21 gene, and FIGS. 4C and 4D show the results of western blotting of p53 protein and p21 protein.

FIGS. 5A and 5B show a change in calcification ability, and FIGS. 5C and 5D show the results of RT-PCR of a hard-tissue marker (ALP, type I collagen, osteopontin).

BEST MODE FOR CARRYING OUT THE INVENTION

Figure 1:
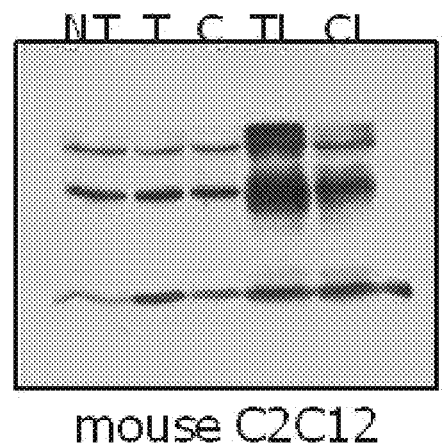
FIG. 1 shows the results of examining the intracellular penetrability of a LMWP-Thioredoxin-1 conjugate.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

As used herein, the term "antioxidant protein" refers to a protein that inhibits the denaturation and loss of function of the proteins by inhibiting reactive oxygen species caused by various factors or converting the oxidation state of proteins caused by oxidative stress into a reduction state. Examples of the antioxidant protein include SOD (superoxide dismutase), thioredoxin, catalase, glutathion peroxidase, heam-containing peroxidase, and analogues thereof.

SOD (superoxide dismutase; SEQ ID NO: 1) functions to protect cells from toxicity by converting superoxide ions, including free radical anions that adversely affect cells, into oxygen and hydrogen peroxide. An antioxidant defense mechanism by this SOD is important in almost all cells that are exposed to oxygen, and some lactic acid bacteria are known to use other defense mechanisms.

Thioredoxin (SEQ ID NO: 2) refers to a low-molecular-weight protein having a molecular weight of 10,000-13,000 and acts as a proton donor when ribonucleotide is reduced by ribonucleotide reductase. It is isolated from *E. coli*. A pair of cysteine residues present in the active center is conserved in prokaryotes and eukaryotes, and thioredoxin has the capability to reduce and cleave the disulfide bond of a target protein in the presence of NADPH and thioredoxin reductase. Human TRX/ADF (human thioredoxin/adult T cell leukemia-derived factor) is involved in cell proliferation or the control of transcription factors.

As used herein, the phrase "protein having the ability to improve cell proliferation" refers to a protein that improves the adaptability of stem cells by engraftment with existing cells after transplantation and facilitates the proliferation of the stem cells. Examples of this protein include HOX4 protein and NF-Ya protein.

HOX4 (homeobox-leucine zipper protein; SEQ ID NO: 3) is a transcription factor that plays an important role in embryo formation. Transcription factors play an important role in the regulation of the expression and differentiation of genes in stem cells and convert various cellular processes by binding to a specific gene target.

NF-Ya (nuclear transcription factor Y subunit alpha; SEQ ID NO: 4) is a major transcription activator of a CCAAT promoter gene and regulates the cell cycle by cellular stress through the p53-depterminalent mechanism of transcriptional inhibition.

The cell-penetrating peptide (CPP) that is used in the present invention is a positively charged peptide and may be selected from the group consisting of (a) LMWP (low molecular weight protamine (SEQ ID NO: 5), (b) TAT (trans activator of transcription (SEQ ID NO: 6), (c) penetratin (SEQ ID NO: 7), (d) polyarginine (6 or more arginines), (e) polylysine (6 or more lysines), (f) a protamine fragment, (g) antennapedia (ANTP), and (h) an oligopeptide comprising 70% or more of histidine, arginine, lysine, or a mixture thereof. In addition, the cell-penetrating peptide (CPP) comprises a protein transduction domain (PTD) and may also be a cell permeable protein.

Although most intracellular drug delivery techniques rely on terminalocytosis that uses receptors on the cell surface, the above peptides carry positive charges, unlike terminalocytosis that is one of intracellular mass transport mechanism, and thus they are attached and transferred depterminaling on the charges of the negatively charged cell membrane and can efficiently introduce desired substances directly into cells within a short time.

As used herein, the phrase "regeneration of stem cells" is meant to include stimulating the differentiation of stem cells, inhibiting apoptosis, improving the ability of stem cells to proliferate, maintaining the functionality of stem cells, and restoring the stress-inhibited functionality of stem cells.

In one aspect, the present invention is directed to a cell permeable fusion protein for intensifying the ability of stem cells to regenerate, the fusion protein comprising a cell permeable peptide linked to the amino terminal of an antioxidant protein or a protein having the ability to improve cell proliferation.

In another aspect, the present invention is directed to a cell permeable fusion protein for improving the ability of stem cells to regenerate or proliferate, the fusion protein comprising a cell permeable peptide linked to the amino terminal of a fusion protein of an antioxidant protein and a protein having the ability to improve cell proliferation.

The inventive fusion protein for improving the ability of stem cells to regenerate or proliferate can be prepared by a chemical or biological method, but is preferably prepared by a biological fusion method that produces fewer by-products. In the chemical fusion method, the amino group of the transcription factor protein is linked to the cell-penetrating peptide by an S—S bond using a crosslinking agent selected from the group consisting of 1,4-bis-maleimidobutane (BMB), 1,11-bis-maleimidotetraethyleneglycol (BM[PEO]4), 1-ethyl-3-[3-dimethyl aminopropyl]carbodiimide hydrochloride (EDC), succinimidyl-4-[N-maleimidomethyl cyclohexane-1-carboxy-[6-amidocaproate]] (SMCC) and sulfo-SMCC, succimidyl 6-[3-(2-pyridyldithio)-ropionamido] hexanoate (SPDP) and sulfo-SPDP, m-maleimidobenzoyl-N-hydroxysuccinimide ester (MBS) and sulfo-MBS, succimidyl[4-(p-maleimidophenyl)butyrate] (SMPB) and sulfo-SMPB. In this case, the peptide binds non-specifically to the amino group of the proteins, causing byproducts comprising a plurality of peptides introduced into one protein. The biological fusion method is designed such that one peptide molecule is introduced in the construction of a plasmid, and thus there is an advantage in that the possibility of production of by-products is low.

In the present invention, the cell permeable fusion protein may be a cell permeable fusion protein for intensifying the regeneration of stem cells, which further comprises a transcription factor protein for inducing osteogenic differentiation, linked to the cell permeable peptide.

As used herein, the phrase "transcription factor protein for inducing osteogenic differentiation" refers to a transcription factor playing a key role in forming skeletal cells from mesenchymal stem cells. Examples of the transcription factor protein include TAZ, Runx2, LMP-1, and derivatives thereof.

TAZ (Tafazzin; SEQ ID NO: 8 or 9) can activate the transcription factor Runx2, which inhibits PPAR-gamma, a transcription factor that induces differentiation into adipocytes, and is essential in the differentiation of mesenchymal stem cells into osteoblasts. In the present invention, TAZ may also mean a gene encoding the TAZ protein.

Runx2 (Runx domain transcription factor 2; SEQ ID NO: 10 or 11) is a transcription factor essential in the differentiation of mesenchymal stem cells into osteoblasts and adipocytes. It induces mesenchymal stem cells to differentiate into osteoblasts or adipocytes. Runx2 is a protein observed to be localized to bone when injected externally, and in addition to this protein, several proteins are known to stimulate the differentiation of cells into bone tissue.

LMP-1 (LIM mineralization protein-1; SEQ ID NO: 12 or 13) also promotes the osteogenic differentiation in cells. Particularly, the present inventors previously confirmed that a specific region of the amino acid sequence (AADPPRYTFAPSVSLNKTARPPGAPPPADSAPQQNG, ADPPRYTFAP, KPQKASAPAADPPRYTFAP) of the LMP-1 protein is associated directly with osteogenic differentiation.

In still another aspect, the present invention is directed to a expression vector of a fusion protein having the ability of stem cells to intensifying regeneration of stem cells, comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines.

The vector that is used in the present invention may be a conventional TA vector or the like, and the expression of the vector is under the control of T7 promoter and LacO-operator.

In yet another aspect, the present invention is directed to a recombinant microorganism transformed with a expression vector of a fusion protein having the ability of stem cells to intensifying regeneration of stem cells, comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines.

A microorganism for transformation that is used in the present invention may be a conventional microorganism, and typical examples thereof, including *E. coli* and the like.

In a further aspect, the present invention is directed to a method for preparing a fusion protein having the ability of stem cells to intensifying regeneration of stem cells, the method comprising the steps of: culturing a recombinant microorganism transformed with a expression vector of a fusion protein having the ability of stem cells to intensifying regeneration of stem cells, comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines, thereby expressing a fusion protein having the ability of stem cells to intensifying regeneration of stem cells; and recovering the expressed fusion protein.

In a still further aspect, the present invention is directed to a method for regeneration of stem cells, the method comprising introducing a fusion protein prepared by a method comprising the steps of: culturing a recombinant microorganism transformed with a expression vector of a fusion protein having the ability of stem cells to intensifying regeneration of stem cells, comprising: a cDNA encoding the transduction domain of a cell permeable peptide; a cDNA encoding the transduction domain of an antioxidant protein and/or a cDNA encoding the transduction domain of a protein having the ability to improve cell proliferation; a cDNA encoding a transcription factor protein for inducing osteogenic differentiation; and a cDNA for 6 histidines, thereby expressing a fusion protein having the ability of stem cells to intensifying regeneration of stem cells; and recovering the expressed fusion protein into stem cells.

In a yet further aspect, the present invention is directed to a cell permeable fusion protein for promoting osteogenesis, the fusion protein comprising a cell permeable peptide linked to the terminal of a fusion protein of an antioxidant protein or a protein having the ability to improve cell proliferation and a transcription factor protein for inducing osteogenic differentiation.

In another further aspect, the present invention is directed to a pharmaceutical composition for treating bone disease, the composition comprising a cell permeable fusion protein for promoting osteogenesis as an active ingredient, the fusion protein comprising a cell permeable peptide linked to the terminal of a fusion protein of an antioxidant protein or a protein having the ability to improve cell proliferation and a transcription factor protein for inducing osteogenic differentiation.

In the present invention, the bone disease may be any one selected from the group consisting of osteoporosis, osteogenesis imperfecta, periodontal disease, and bone fracture.

The pharmaceutical composition for treating bone disease can be administered orally or non-orally (intramuscular, intravenous, suppository, etc.). The preferred dosage of the pharmaceutical composition for treating bone disease of the present invention can be suitably adjusted depterminaling on the patient's conditions, for example, age and the severity of disease. In order to achieve the desired effects, however, for adults, the pharmaceutical composition of the present invention may be administered at a daily dose of from 100 to 1,000 mg/day, and preferably 300 to 1,000 mg/day within a dose range of from 100 to 50 mg/day. The pharmaceutical composition may be administered in a single dose per day or in multiple doses per day.

When the pharmaceutical composition for treating bone disease according to the present invention is formulated as an oral dosage form, the formulation can be prepared by adding an excipient, optionally a binder, a disintegrant, a lubricant, a colorant, a flavor enhancer or the like to the composition, and then preparing the mixture into a tablet, a coated tablet, a granule formulation, a capsule or the like according to a conventional method.

Examples of carrier, excipient or diluent that can be used in the pharmaceutical composition for treating bone disease may include lactose, corn starch, white sugar, glucose, lactose, dextrose, sucrose, sorbitol, crystalline cellulose, mannitol, xylitol, erythritol, maltitol, acacia rubber, alginate, gelatin, calcium phosphate, calcium silicate, polyvinylpyrrolidone, water, methylhydroxybenzoate, propylhydroxybenzoate, talc, magnesium stearate, and mineral oils. Examples of the binder which can be used in the pharmaceutical composition for treating bone disease may include polyvinyl alcohol, polyvinyl ether, ethyl cellulose, methyl cellulose, Arabic gum, gelatin, (shellac), hydroxyprophyl cellulose, hydroxyprophyl starch, and polyvinyl pyridine. In addition, Examples of the disintegrant which can be used in the pharmaceutical composition for treating bone disease may include starch, agar, gelatin powder, crystalline cellulose, calcium carbonate, sodium hydrogen carbonate, calcium citrate, dextran, and pectin. Examples of the lubricant which can be used in the pharmaceutical composition for treating bone disease may include stearic acid, magnesium, talc, polyethylene glycol, silica, and vegetable oils. A colorant that can be used in the pharmaceutical composition for treating bone disease may be one approved for use in medical applications, and a flavor enhancer that can be used in the pharmaceutical composition may be cocoa powder, menthol, aromatic acid, mint oil, borneol, cinnamon powder or the like.

In addition, when the pharmaceutical composition for treating bone disease according to the present invention is formulated as an injectable dosage form, the formulation can be prepared by adding a pH adjusting agent, a buffer, a stabilizer, a preservative or the like the composition and formulating the mixture into an injectable liquid for subcutaneous, intramuscular or intravenous injection according to a conventional method.

The pharmaceutical composition for treating bone disease of the present invention may be administered by various routes into mammals, including rats, mice, livestock and humans. All routes of administration can be contemplated and include, for example, oral, rectal or intravenous, intramuscular, subcutaneous, intrauterine, intrathecal or intracerebrovascular injections.

In another still further aspect, the present invention is directed to a health functional food for treating bone disease, comprising a cell permeable fusion protein for promoting osteogenesis, the fusion protein comprising a cell permeable peptide linked to the terminal of a fusion protein of an antioxidant protein or a protein having the ability to improve cell proliferation and a transcription factor protein for inducing osteogenic differentiation as an active ingredient and further comprising an acceptable food additive.

As used herein, the term "functional food" refers to a food, the functionality of which has been improved by adding thereto a cell permeable fusion protein for promoting osteogenesis (CPP-TAZ) according to the present invention, to conventional food.

In addition, the health functional food for treating bone disease of the present invention may further contain various nutrients, vitamins, minerals (electrolytes), seasonings (artificial seasonings and natural seasonings), coloring agents and improving agents (cheese, chocolate and the like), pectic acid and salts thereof, alginic acid and salts thereof, organic acids, protective colloid thickeners, pH controllers, stabilizers, preservatives, glycerin, alcohols, carbonating agents used in carbonated beverages, and the like as acceptable food additives.

In addition, the health functional food for treating bone disease of the present invention may further contain fruit flesh for preparation of natural fruit juice beverages, fruit juice beverages and vegetable beverages. These additives may be used indepterminalently or in combination. Although the content of these additives in the health functional food for treating bone disease of the present invention is not particularly limited, it is generally selected within the range of 0.01-20 parts by weight based on 100 parts by weight of the cell permeable fusion protein for promoting osteogenesis of the present invention.

In particular, an example of the present example illustrated that, when stem cells are treated with a fusion protein of LMWP with thioredoxin or SOD, the ability of the stem cells to regenerate or proliferate was improved. However, it will be obvious to one skilled in the art from the disclosure of the present invention that a fusion protein of a conventional cell permeable peptide with an antioxidant protein improves the ability of stem cells to regenerate or proliferate, and thus falls within the scope of the present invention.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Recombinant LMWP-Thoredoxin-1 Fusion Protein and Examination of the Ability Thereof to Penetrate Cells An LMWP peptide was synthesized, and then conjugated with thioredoxin (1 mg/ml in PBS) using SMCC (Pierce). The LMWP-thioredoxin conjugate was purified using a heparin-agarose bead (Sigma).

A C2C12 model cell line (ATCC) was cultured in serum-free medium for 24 hours under the conditions of 95% air, 5% $CO_2$ and 37° C. Next, the model cell line (mouse C2C12) was treated with the LMWP-Trx-1 (WT and C3134S) conjugates and incubated in serum-free medium for 30 min, and then an experiment for comparison of the conjugates with non-conjugated thioredoxin-1 was performed. As a result, it was shown that the ability of the conjugates to penetrate the cells was excellent compared to that of thioredoxin-1 alone, the ability of WT conjugate to penetrate the cells was superior to that of the C3134S conjugate (see FIG. 1).

Example 2

Figure 2:
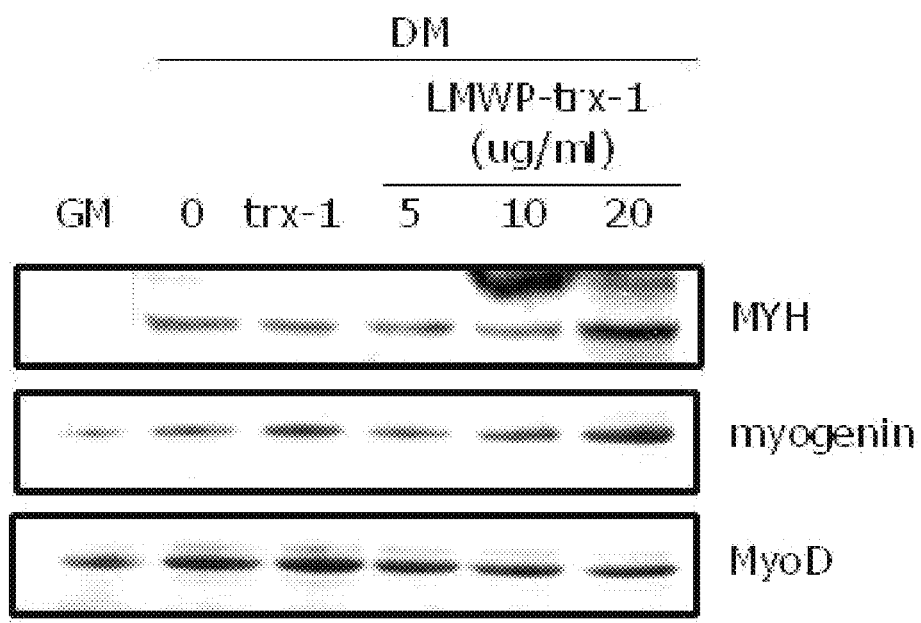
FIG. 2 shows the results of examining the in vivo functionality of a LMWP-Thioredoxin-1 conjugate.

Examination of the Ability of Recombinant LMWP-Thoredoxin-1 Fusion Protein to Stimulate the Differentiation of Stem Cells In order to examine the influence of the LMWP-thioredoxin-1 fusion protein on the differentiation of stem cells (Lonza) into myocytes, stem cells were treated with the LMWP-thioredoxin-1-WT conjugate according to the concentration and incubated under the conditions of 95% air, 5% $CO_2$ and 37° C. Then, the expression levels of MYH, Myogenin and MyoD proteins (myocyte differentiation markers) in the cells were analyzed by a Western blotting technique. In this experiment, thioredoxin-1 not conjugated with LMWP was used as a control. As a result, it was shown that, when the cells were treated with the LMWP-thioredoxin-1-WT conjugate, the differentiation of the cells into myocytes increased in a concentration-depterminalent manner (see FIG. 2).

Example 3

Preparation of Recombinant LMWP-SOD Fusion Protein and Examination of the Ability Thereof to Inhibit Apoptosis A LMWP peptide was synthesized, and then conjugated with SOD (Sigma, 1 mg/ml in PBS) using SMCC (Pierce). The LMWP-SOD conjugate was purified using a heparin-agarose bead (Sigma).

Figure 3:
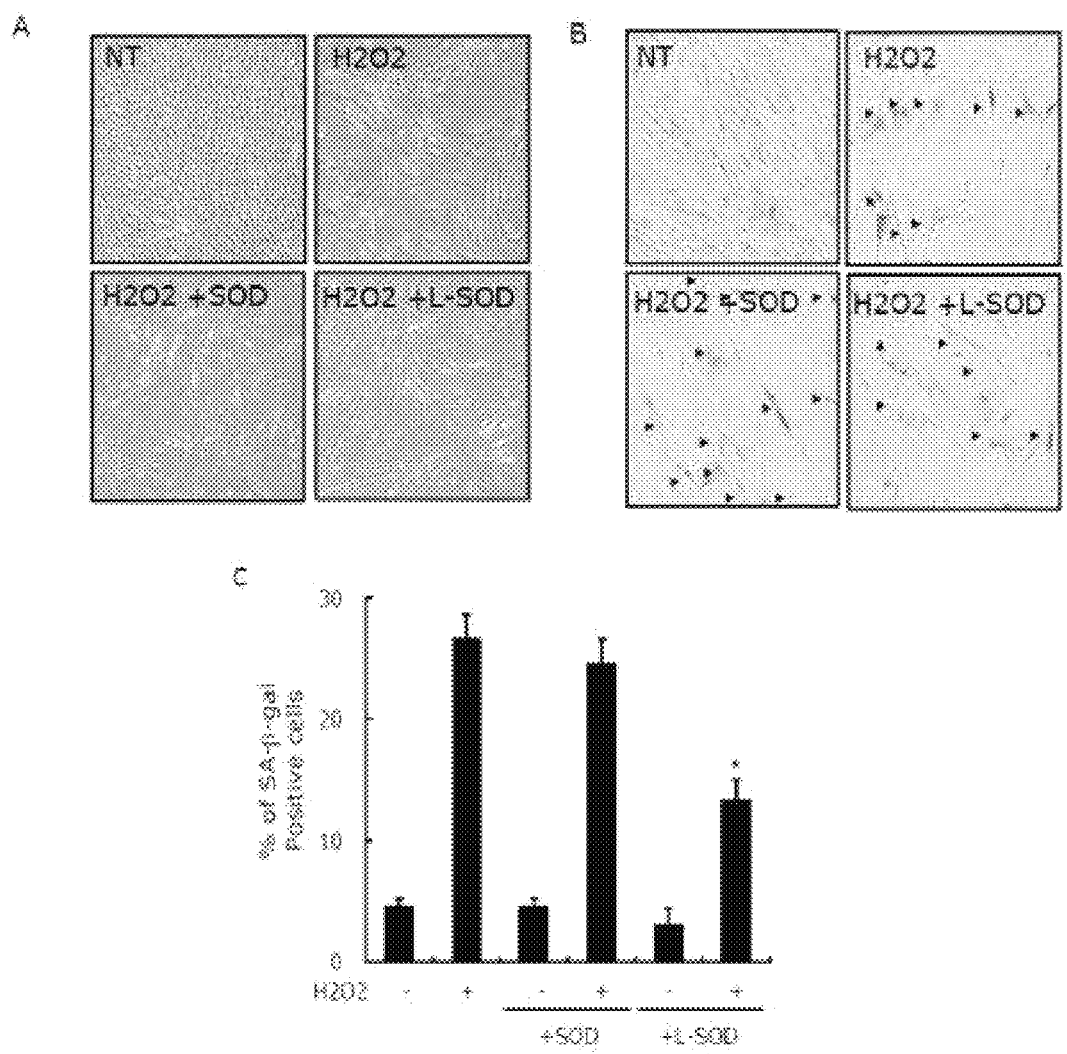
FIG. 3 shows the results of examining the ability to inhibit senescence of a LMWP-SOD fusion protein.

Analysis was carried out to examine the influence of the LMWP-SOD fusion protein having the ability to penetrate cells on apoptosis. Specifically, human dental pulp stem cells (primary culture) were seeded into a 6-well plate at a density of $1 \times 10^4$ cells per well, and then cultured under the conditions of 95% air, 5% $CO_2$ and 37° C. for 24 hours. Next, the cells were treated with varying concentrations of the LMWP-SOD conjugate and incubated for 2 hours. Then, the cells were treated with a low concentration (150 uM) of hydrogen peroxide in serum-free medium for 2 hours to artificially induce cell senescence, and then incubated in general medium for 3 days. The degree of senescence of the cells was examined by a cellular morphological change (see FIG. 3A) and senescence-associated beta-galactosidase staining (see FIGS. 3B and 3C). As a result, it could be seen that, in the test group pretreated with LMWP-SOD, the flatten morphology of the cells was partially restored and SA-beta-gal staining definitely decreased.

Example 4

Figure 4:
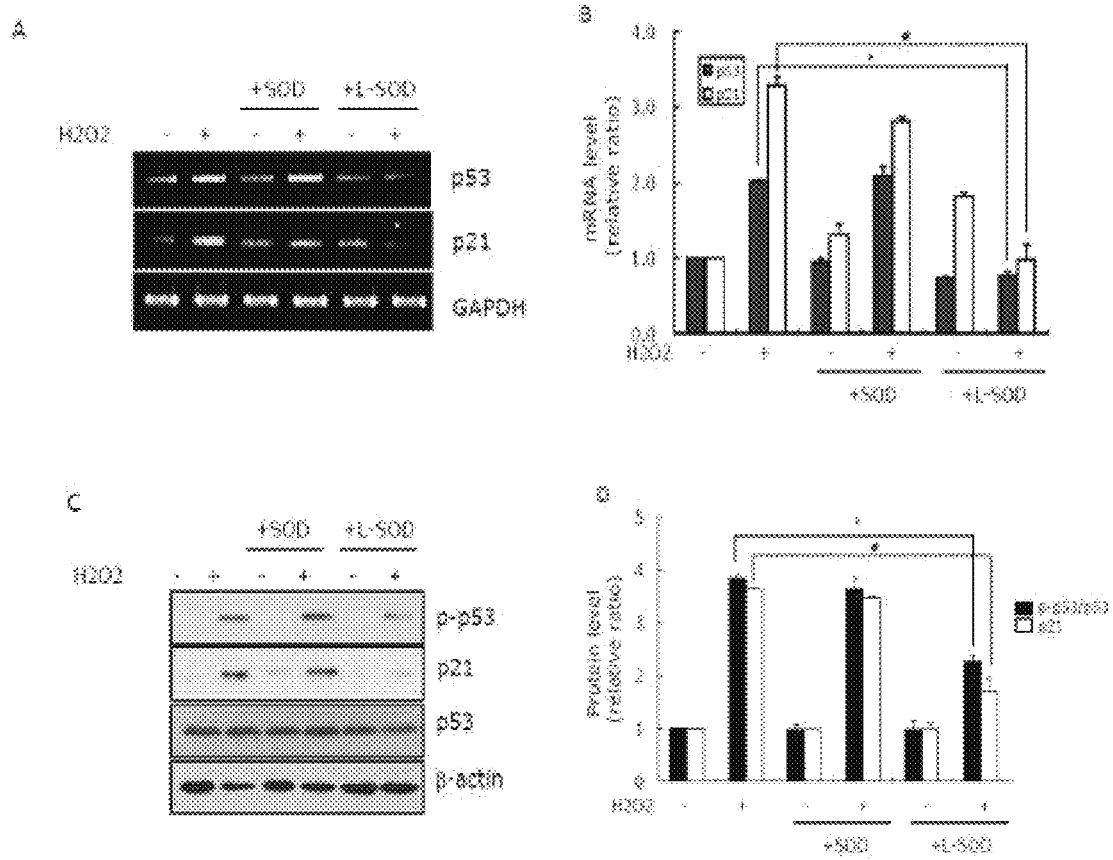
FIG. 4 shows the examining the ability to inhibit senescence of a LMWP-SOD fusion protein.

Examination of the Ability of Recombinant LMWP-SOD Fusion Protein to Maintain the Functionality of Stem Cells and Examination of Proteins that are Involved in the Maintenance Analysis was performed to examine the influence of the LMWP-SOD conjugate having the ability to penetrate cells on the functionality of stem cells. Specifically, human dental pulp stem cells were seeded into a 100-mm dish at a density of $1 \times 10^6$ cells, and then cultured for 24 hours. Next, the cells were treated with varying concentrations of the LMWP-SOD conjugate and incubated for 2 hours under the conditions of 95% air, 5% $CO_2$ and 37° C. Then, the cells were treated with a low concentration (150 uM) of hydrogen peroxide in serum-free medium for 2 hours to artificially induce cellular stress, and then incubated in general medium for 3 days. Changes in the p53 gene and protein known to be involved in cellular senescence, and the p21 gene and protein whose activity is regulated by p53, were analyzed by RT-PCR (see FIGS. 4A and 4B) and a Western blotting technique (see FIGS. 4C and 4D). As a result, it could be seen that, in the test group pretreated with LMWP-SOD, the expression levels of the p53 and p21 genes decreased and the expression levels of the proteins also significantly decreased. In this experiment, it was found that the introduction of the physiologically active peptide, which is not toxic and can function to efficiently deliver a specific protein into cells, increases the expression of the SOD protein required to inhibit cellular senescence, thereby inhibiting cellular stress caused by hydrogen peroxide, and p53/p21 signaling pathways are involved in this inhibition process.

Example 5

Figure 5:
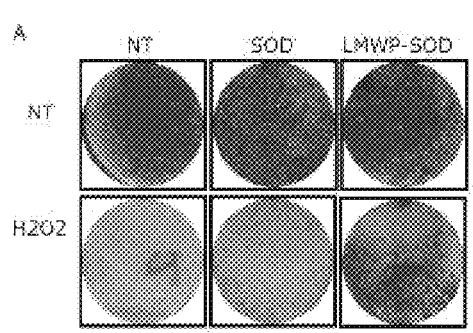
FIG. 5 shows the results of examining the restoration of functionality of stem cell by a LMWP-SOD fusion protein.
Figure 5:
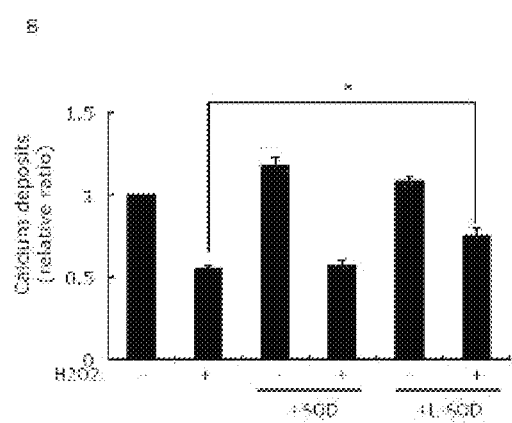
Figure 5:
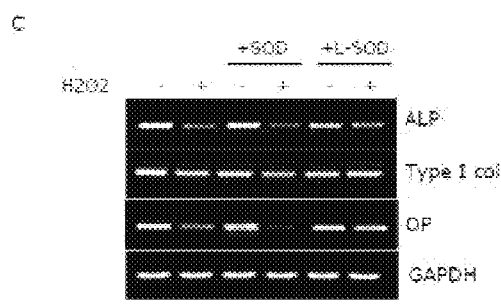
Figure 5:
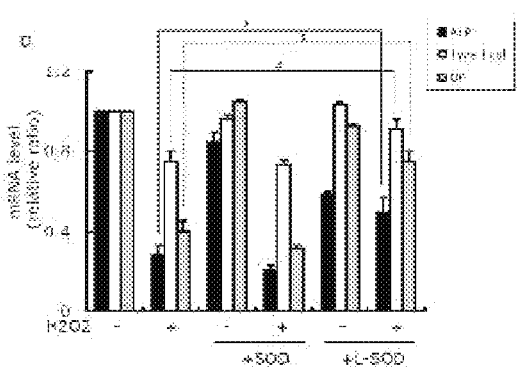

Restoration of Functionality of Stem Cells Stress-Inhibited by Recombinant LMWP-SOD Fusion Protein When stem cells undergo stress due to a change in the surrounding environment, the stem cells lose their functionality. In this experiment, from this viewpoint, the degree of mineralization was measured by Alizarin red S staining to determine whether the LMWP-SOD conjugate can penetrate into aged stem cells (Lonza) to restore the functionality of the cells. Specifically, stem cells were treated with the LMWP-SOD conjugate, and after 2 hours, treated with hydrogen peroxide, followed by incubation under the conditions of 95% air, 5% $CO_2$ and 37° C. for 14 days. Following this, the degree of mineralization of the cells was measured by Alizarin red S staining. As a result, it was shown that the mineralization of the group treated with LMWP-SOD was restored, unlike the group treated with SOD alone or the control group (see FIGS. 5A and 5B). In order to confirm this effect of restoring the functionality of stem cells, the mRNA levels of ALP, type I collagen, osteopontin, which are hard-tissue differentiation genes, were analyzed. As a result, it was shown that the expression levels of these genes in the group treated with LMWP-SOD were restored in a pattern similar to that of FIGS. 5A and 5B (see FIGS. 5C and 5D).

Although the present invention has been described in detail with reference to the specific features, it will be apparent to those skilled in the art that this description is only for a preferred embodiment and does not limit the scope of the present invention. Thus, the substantial scope of the present invention will be defined by the appterminaled claims and equivalents thereof.

INDUSTRIAL APPLICABILITY

According to the present invention, when stem cells are treated with the cell permeable fusion protein for intensifying the regeneration of stem cells, it easily penetrates the stem cells to stimulate the differentiation of the stem cells, to inhibit apoptosis, to maintain the functionality of the cells and to promote the restoration of stress-inhibited functionality of the stem cells. Thus, the fusion protein is useful for the regeneration of stem cells.

---

The invention claimed is:

1. A cell permeable fusion protein for improving an ability to regenerate or proliferate stem cells, wherein a cell permeable peptide is linked to the amino terminal of Thioredoxin antioxidant protein, wherein the cell permeable peptide is LMWP (low molecular weight protamine) (SEQ ID NO: 5).

2. The cell permeable fusion protein for improving an ability to regenerate or proliferate stem cells of claim 1, wherein a transcription factor protein having an functionality of osteogenic differentiation is further linked to the cell permeable fusion protein.

3. The cell permeable fusion protein for improving an ability to regenerate or proliferate stem cells of claim 1, wherein the Thioredoxin is represented by SEQ ID NO: 2.

4. An expression vector of the permeable fusion protein for improving an ability to regenerate or proliferate stem cells according to claim 1, wherein the vector comprises: a cDNA encoding the transduction domain of the LMWP (low molecular weight protamine); a cDNA encoding the transduction domain of the thioredoxin protein.

5. A recombinant microorganism transformed with the expression vector of claim 4.

6. A method for preparing a fusion protein for improving an ability to regenerate or proliferate stem cells, wherein the method comprises the steps of:

culturing the recombinant microorganism of claim 5, thereby expressing the fusion protein for improving an ability to regenerate or proliferate stem cells; and recovering the expressed fusion protein.

7. A method for regeneration of stem cells, wherein the method comprises introducing the fusion protein prepared by the method of claim 6 into stem cells.

8. A cell permeable fusion protein for promoting osteogenesis, wherein a cell permeable peptide is linked to the terminal of a fusion protein of Thioredoxin antioxidant protein and a transcription factor protein having functionality of osteogenic differentiation, wherein the cell permeable peptide is LMWP (low molecular weight protamine) (SEQ ID NO: 5).

9. A pharmaceutical composition for treating bone disease, the composition comprising the cell permeable fusion protein for promoting osteogenesis of claim 8 as an active ingredient.

10. The pharmaceutical composition for treating bone disease of claim 9, wherein the bone disease is any one selected from the group consisting of osteoporosis, osteogenesis imperfecta, periodontal disease and bone fracture.

11. A health functional food for treating bone disease comprising the cell permeable fusion protein for promoting osteogenesis of claim 8 as an active ingredient.

* * * * *

SEQUENCE LISTING

```
<160> NUMBER OF SEQ ID NOS: 12

<210> SEQ ID NO 1
<211> LENGTH: 153
<212> TYPE: PRT
<213> ORGANISM: Artificial
<220> FEATURE:
<223> OTHER INFORMATION: SOD-HUMAN

<400> SEQUENCE: 1

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 2
<211> LENGTH: 103
<212> TYPE: PRT
<213> ORGANISM: Artificial
<220> FEATURE:
<223> OTHER INFORMATION: Thioredoxin-HUMAN
```

```
<400> SEQUENCE: 2

Val Lys Gln Ile Glu Ser Lys Thr Ala Phe Gln Glu Ala Leu Asp Ala
1               5                   10                  15

Ala Gly Asp Lys Leu Val Val Asp Phe Ser Ala Thr Trp Cys Gly
            20                  25                  30

Pro Cys Lys Met Ile Lys Pro Phe His Ser Leu Ser Glu Lys Tyr
        35                  40                  45

Ser Asn Val Ile Phe Leu Glu Val Asp Val Asp Cys Gln Asp Val
    50                  55                  60

Ala Ser Glu Cys Glu Val Lys Cys Met Pro Thr Phe Gln Phe Phe Lys
65                  70                  75                  80

Lys Gly Gln Lys Val Gly Glu Phe Ser Gly Ala Asn Lys Glu Lys Leu
            85                  90                  95

Glu Ala Thr Ile Asn Glu Leu
                100

<210> SEQ ID NO 3
<211> LENGTH: 277
<212> TYPE: PRT
<213> ORGANISM: Artificial
<220> FEATURE:
<223> OTHER INFORMATION: HOX4

<400> SEQUENCE: 3

Met Lys Arg Pro Gly Gly Ala Gly Gly Gly Gly Ser Pro Ser Leu
1               5                   10                  15

Val Thr Met Ala Asn Ser Ser Asp Asp Gly Tyr Gly Gly Val Gly Met
            20                  25                  30

Glu Ala Glu Gly Asp Val Glu Glu Met Met Ala Cys Gly Gly Gly
            35                  40                  45

Gly Glu Lys Lys Arg Arg Leu Ser Val Glu Gln Val Arg Ala Leu Glu
        50                  55                  60

Arg Ser Phe Glu Val Glu Asn Lys Leu Glu Pro Glu Arg Lys Ala Arg
65                  70                  75                  80

Leu Ala Arg Asp Leu Gly Leu Gln Pro Arg Gln Val Ala Val Trp Phe
            85                  90                  95

Gln Asn Arg Arg Ala Arg Trp Lys Thr Lys Gln Leu Glu Arg Asp Tyr
            100                 105                 110

Ala Ala Leu Arg His Ser Tyr Asp Ser Leu Arg Leu His Asp Ala
        115                 120                 125

Leu Arg Arg Asp Lys Asp Ala Leu Leu Ala Glu Ile Lys Glu Leu Lys
130                 135                 140

Ala Lys Leu Gly Asp Glu Glu Ala Ala Ser Phe Thr Ser Val Lys
145                 150                 155                 160

Glu Glu Pro Ala Ala Ser Asp Gly Pro Pro Ala Ala Gly Phe Gly Ser
                165                 170                 175

Ser Asp Ser Asp Ser Ser Ala Val Leu Asn Asp Val Ala Ala Gly
        180                 185                 190

Ala Ala Pro Ala Ala Thr Asp Ala Leu Ala Pro Glu Ala Cys Thr Phe
            195                 200                 205

Leu Gly Ala Pro Pro Ala Gly Ala Gly Ala Ala Ala Ala
        210                 215                 220

Ala Ser His Glu Glu Val Phe Phe His Gly Asn Phe Leu Lys Val Glu
225                 230                 235                 240

Glu Asp Glu Thr Gly Phe Leu Asp Asp Asp Glu Pro Cys Gly Gly Phe
```

```
                245                 250                 255
Phe Ala Asp Asp Gln Pro Pro Leu Ser Ser Trp Trp Ala Glu Pro
            260                 265                 270
Thr Glu His Trp Asn
        275

<210> SEQ ID NO 4
<211> LENGTH: 347
<212> TYPE: PRT
<213> ORGANISM: Artificial
<220> FEATURE:
<223> OTHER INFORMATION: NF-Ya

<400> SEQUENCE: 4

Met Glu Gln Tyr Thr Ala Asn Ser Asn Ser Thr Glu Gln Ile Val
1               5                   10                  15

Val Gln Ala Gly Gln Ile Gln Gln Gln Gln Gly Val Thr Ala
            20                  25                  30

Val Gln Leu Gln Thr Glu Ala Gln Val Ala Ser Ala Ser Gly Gln Gln
            35                  40                  45

Val Gln Thr Leu Gln Val Val Gln Gly Gln Pro Leu Met Val Gln Val
50                  55                  60

Ser Gly Gly Gln Leu Ile Thr Ser Thr Gly Gln Pro Ile Met Val Gln
65                  70                  75                  80

Ala Val Pro Gly Gly Gln Gly Gln Thr Ile Met Gln Val Pro Val Ser
                85                  90                  95

Gly Thr Gln Gly Leu Gln Gln Ile Gln Leu Val Pro Pro Gly Gln Ile
                100                 105                 110

Gln Ile Gln Gly Gly Gln Ala Val Gln Val Gln Gly Gln Gln Gly Gln
            115                 120                 125

Thr Gln Gln Ile Ile Ile Gln Gln Pro Gln Thr Ala Val Thr Ala Gly
130                 135                 140

Gln Thr Gln Thr Gln Gln Gln Ile Ala Val Gln Gly Gln Gln Val Ala
145                 150                 155                 160

Gln Thr Ala Glu Gly Gln Thr Ile Val Tyr Gln Pro Val Asn Ala Asp
                165                 170                 175

Gly Thr Ile Leu Gln Gln Val Thr Val Pro Val Ser Gly Met Ile Thr
                180                 185                 190

Ile Pro Ala Ala Ser Leu Ala Gly Ala Gln Ile Val Gln Thr Gly Ala
            195                 200                 205

Asn Thr Asn Thr Thr Ser Ser Gly Gln Gly Thr Val Thr Val Thr Leu
210                 215                 220

Pro Val Ala Gly Asn Val Val Asn Ser Gly Gly Met Val Met Met Val
225                 230                 235                 240

Pro Gly Ala Gly Ser Val Pro Ala Ile Gln Arg Ile Pro Leu Pro Gly
                245                 250                 255

Ala Glu Met Leu Glu Glu Glu Pro Leu Tyr Val Asn Ala Lys Gln Tyr
                260                 265                 270

His Arg Ile Leu Lys Arg Arg Gln Ala Arg Ala Lys Leu Glu Ala Glu
            275                 280                 285

Gly Lys Ile Pro Lys Glu Arg Arg Lys Tyr Leu His Glu Ser Arg His
            290                 295                 300

Arg His Ala Met Ala Arg Lys Arg Gly Glu Gly Gly Arg Phe Phe Ser
305                 310                 315                 320

Pro Lys Glu Lys Asp Ser Pro His Met Gln Asp Pro Asn Gln Ala Asp
```

```
                            325                 330                 335

Glu Glu Ala Met Thr Gln Ile Ile Arg Val Ser
            340                 345

<210> SEQ ID NO 5
<211> LENGTH: 15
<212> TYPE: PRT
<213> ORGANISM: Artificial
<220> FEATURE:
<223> OTHER INFORMATION: TAT(Transactivator of Transcription Peptide
      from HIV type-1)

<400> SEQUENCE: 5

Cys Gly Arg Lys Lys Arg Arg Gln Arg Arg Pro Pro Gln Cys
1               5                   10                  15

<210> SEQ ID NO 6
<211> LENGTH: 16
<212> TYPE: PRT
<213> ORGANISM: Artificial
<220> FEATURE:
<223> OTHER INFORMATION: Penetratin

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 400
<212> TYPE: PRT
<213> ORGANISM: Artificial
<220> FEATURE:
<223> OTHER INFORMATION: TAZ-HUMAN

<400> SEQUENCE: 7

Met Asn Pro Ala Ser Ala Pro Pro Pro Leu Pro Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Ser Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140

His Ile Glu Lys Ile Thr Thr Trp Gln Asp Pro Arg Lys Ala Met Asn
145                 150                 155                 160

Gln Pro Leu Asn His Met Asn Leu His Pro Ala Val Ser Ser Thr Pro
                165                 170                 175

Val Pro Gln Arg Ser Met Ala Val Ser Gln Pro Asn Leu Val Met Asn
            180                 185                 190

His Gln His Gln Gln Gln Met Ala Pro Ser Thr Leu Ser Gln Gln Asn
```

```
            195                 200                 205
His Pro Thr Gln Asn Pro Pro Ala Gly Leu Met Ser Met Pro Asn Ala
210                 215                 220

Leu Thr Thr Gln Gln Gln Gln Gln Lys Leu Arg Leu Gln Arg Ile
225                 230                 235                 240

Gln Met Glu Arg Glu Arg Ile Arg Met Arg Gln Glu Glu Leu Met Arg
                    245                 250                 255

Gln Glu Ala Ala Leu Cys Arg Gln Leu Pro Met Glu Ala Glu Thr Leu
                260                 265                 270

Ala Pro Val Gln Ala Ala Val Asn Pro Pro Thr Met Thr Pro Asp Met
            275                 280                 285

Arg Ser Ile Thr Asn Asn Ser Ser Asp Pro Phe Leu Asn Gly Gly Pro
290                 295                 300

Tyr His Ser Arg Glu Gln Ser Thr Asp Ser Gly Leu Gly Leu Gly Cys
305                 310                 315                 320

Tyr Ser Val Pro Thr Thr Pro Glu Asp Phe Leu Ser Asn Val Asp Glu
                    325                 330                 335

Met Asp Thr Gly Glu Asn Ala Gly Gln Thr Pro Met Asn Ile Asn Pro
                340                 345                 350

Gln Gln Thr Arg Phe Pro Asp Phe Leu Asp Cys Leu Pro Gly Thr Asn
            355                 360                 365

Val Asp Leu Gly Thr Leu Glu Ser Glu Asp Leu Ile Pro Leu Phe Asn
370                 375                 380

Asp Val Glu Ser Ala Leu Asn Lys Ser Glu Pro Phe Leu Thr Trp Leu
385                 390                 395                 400

<210> SEQ ID NO 8
<211> LENGTH: 395
<212> TYPE: PRT
<213> ORGANISM: Artificial
<220> FEATURE:
<223> OTHER INFORMATION: TAZ-MOUSE

<400> SEQUENCE: 8

Met Asn Pro Ser Ser Val Pro His Pro Leu Pro Pro Gly Gln Gln
1               5                   10                  15

Val Ile His Val Thr Gln Asp Leu Asp Thr Asp Leu Glu Ala Leu Phe
                20                  25                  30

Asn Ser Val Met Asn Pro Lys Pro Ser Ser Trp Arg Lys Lys Ile Leu
                35                  40                  45

Pro Glu Ser Phe Phe Lys Glu Pro Asp Ser Gly Ser His Ser Arg Gln
            50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Gly Pro Ala Gln Gln His Ala His
                100                 105                 110

Leu Arg Gln Gln Ser Tyr Asp Val Thr Asp Glu Leu Pro Leu Pro Pro
            115                 120                 125

Gly Trp Glu Met Thr Phe Thr Ala Thr Gly Gln Arg Tyr Phe Leu Asn
            130                 135                 140

His Ile Glu Lys Ile Thr Thr Trp Gln Asp Pro Arg Lys Val Met Asn
145                 150                 155                 160

Gln Pro Leu Asn His Val Asn Leu His Pro Ser Ile Thr Ser Thr Ser
```

```
                165                 170                 175
Val Pro Gln Arg Ser Met Ala Val Ser Gln Pro Asn Leu Ala Met Asn
            180                 185                 190

His Gln His Gln Gln Val Val Ala Thr Ser Leu Ser Pro Gln Asn His
            195                 200                 205

Pro Thr Gln Asn Gln Pro Thr Gly Leu Met Ser Val Pro Asn Ala Leu
            210                 215                 220

Thr Thr Gln Gln Gln Gln Gln Lys Leu Arg Leu Gln Arg Ile Gln
225                 230                 235                 240

Met Glu Arg Glu Arg Ile Arg Met Arg Gln Glu Leu Met Arg Gln
                245                 250                 255

Glu Ala Ala Leu Cys Arg Gln Leu Pro Met Glu Thr Glu Thr Met Ala
                260                 265                 270

Pro Val Asn Thr Pro Ala Met Ser Thr Asp Met Arg Ser Val Thr Asn
            275                 280                 285

Ser Ser Ser Asp Pro Phe Leu Asn Gly Gly Pro Tyr His Ser Arg Glu
            290                 295                 300

Gln Ser Thr Asp Ser Gly Leu Gly Leu Gly Cys Tyr Ser Val Pro Thr
305                 310                 315                 320

Thr Pro Glu Asp Phe Leu Ser Asn Met Asp Glu Met Asp Thr Gly Glu
                325                 330                 335

Asn Ser Gly Gln Thr Pro Met Thr Val Asn Pro Gln Thr Arg Phe
            340                 345                 350

Pro Asp Phe Leu Asp Cys Leu Pro Gly Thr Asn Val Asp Leu Gly Thr
            355                 360                 365

Leu Glu Ser Glu Asp Leu Ile Pro Leu Phe Asn Asp Val Glu Ser Ala
370                 375                 380

Leu Asn Lys Ser Glu Pro Phe Leu Thr Trp Leu
385                 390                 395
```

<210> SEQ ID NO 9
<211> LENGTH: 521
<212> TYPE: PRT
<213> ORGANISM: Artificial
<220> FEATURE:
<223> OTHER INFORMATION: RUNX-HUMAN

<400> SEQUENCE: 9

```
Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
            35                  40                  45

Gln Gln Gln Gln Gln Gln Gln Gln Gln Gln Gln Gln Gln Gln Gln
50                  55                  60

Gln Gln Gln Gln Gln Gln Gln Glu Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
                100                 105                 110

Leu Val Arg Thr Asp Ser Pro Asn Phe Leu Cys Ser Val Leu Pro Ser
            115                 120                 125

His Trp Arg Cys Asn Lys Thr Leu Pro Val Ala Phe Lys Val Val Ala
```

```
            130                 135                 140
Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
            180                 185                 190

Arg Gly Lys Ser Phe Thr Leu Thr Ile Thr Val Phe Thr Asn Pro Pro
        195                 200                 205

Gln Val Ala Thr Tyr His Arg Ala Ile Lys Val Thr Val Asp Gly Pro
    210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255

Met Arg Val Gly Val Pro Pro Gln Asn Pro Arg Pro Ser Leu Asn Ser
            260                 265                 270

Ala Pro Ser Pro Phe Asn Pro Gln Gly Gln Ser Gln Ile Thr Asp Pro
        275                 280                 285

Arg Gln Ala Gln Ser Ser Pro Pro Trp Ser Tyr Asp Gln Ser Tyr Pro
    290                 295                 300

Ser Tyr Leu Ser Gln Met Thr Ser Pro Ser Ile His Ser Thr Thr Pro
305                 310                 315                 320

Leu Ser Ser Thr Arg Gly Thr Gly Leu Pro Ala Ile Thr Asp Val Pro
                325                 330                 335

Arg Arg Ile Ser Asp Asp Asp Thr Ala Thr Ser Asp Phe Cys Leu Trp
            340                 345                 350

Pro Ser Thr Leu Ser Lys Lys Ser Gln Ala Gly Ala Ser Glu Leu Gly
        355                 360                 365

Pro Phe Ser Asp Pro Arg Gln Phe Pro Ser Ile Ser Ser Leu Thr Glu
    370                 375                 380

Ser Arg Phe Ser Asn Pro Arg Met His Tyr Pro Ala Thr Phe Thr Tyr
385                 390                 395                 400

Thr Pro Pro Val Thr Ser Gly Met Ser Leu Gly Met Ser Ala Thr Thr
                405                 410                 415

His Tyr His Thr Tyr Leu Pro Pro Tyr Pro Gly Ser Ser Gln Ser
        420                 425                 430

Gln Ser Gly Pro Phe Gln Thr Ser Ser Thr Pro Tyr Leu Tyr Tyr Gly
    435                 440                 445

Thr Ser Ser Gly Ser Tyr Gln Phe Pro Met Val Pro Gly Gly Asp Arg
450                 455                 460

Ser Pro Ser Arg Met Leu Pro Pro Cys Thr Thr Thr Ser Asn Gly Ser
465                 470                 475                 480

Thr Leu Leu Asn Pro Asn Leu Pro Asn Gln Asn Asp Gly Val Asp Ala
                485                 490                 495

Asp Gly Ser His Ser Ser Ser Pro Thr Val Leu Asn Ser Ser Gly Arg
            500                 505                 510

Met Asp Glu Ser Val Trp Arg Pro Tyr
        515                 520

<210> SEQ ID NO 10
<211> LENGTH: 607
<212> TYPE: PRT
<213> ORGANISM: Artificial
```

<220> FEATURE:
<223> OTHER INFORMATION: RUNX-MOUSE

<400> SEQUENCE: 10

```
Met Leu His Ser Pro His Lys Gln Pro Gln Asn His Lys Cys Gly Ala
1               5                   10                  15

Asn Phe Leu Gln Glu Asp Cys Lys Lys Ala Leu Ala Phe Lys Trp Leu
            20                  25                  30

Ile Ser Ala Gly His Tyr Gln Pro Pro Arg Pro Thr Glu Ser Val Ser
        35                  40                  45

Ala Leu Thr Thr Val His Ala Gly Ile Phe Lys Ala Ala Ser Ser Ile
    50                  55                  60

Tyr Asn Arg Gly His Lys Phe Tyr Leu Glu Lys Lys Gly Gly Thr Met
65                  70                  75                  80

Ala Ser Asn Ser Leu Phe Ser Ala Val Thr Pro Cys Gln Gln Ser Phe
                85                  90                  95

Phe Trp Asp Pro Ser Thr Ser Arg Arg Phe Ser Pro Pro Ser Ser Ser
            100                 105                 110

Leu Gln Pro Gly Lys Met Ser Asp Val Ser Pro Val Val Ala Ala Gln
        115                 120                 125

Gln Gln Gln Gln Gln Gln Gln Gln Gln Gln Gln Gln Gln Gln Gln Gln
    130                 135                 140

Gln Gln Gln Gln Gln Gln Gln Gln Gln Gln Glu Ala Ala Ala
145                 150                 155                 160

Ala Ala Ala Ala Ala Ala Ala Ala Ala Ala Ala Ala Ala Ala Ala Val
                165                 170                 175

Pro Arg Leu Arg Pro Pro His Asp Asn Arg Thr Met Val Glu Ile Ile
            180                 185                 190

Ala Asp His Pro Ala Glu Leu Val Arg Thr Asp Ser Pro Asn Phe Leu
        195                 200                 205

Cys Ser Val Leu Pro Ser His Trp Arg Cys Asn Lys Thr Leu Pro Val
    210                 215                 220

Ala Phe Lys Val Val Ala Leu Gly Glu Val Pro Asp Gly Thr Val Val
225                 230                 235                 240

Thr Val Met Ala Gly Asn Asp Glu Asn Tyr Ser Ala Glu Leu Arg Asn
                245                 250                 255

Ala Ser Ala Val Met Lys Asn Gln Val Ala Arg Phe Asn Asp Leu Arg
            260                 265                 270

Phe Val Gly Arg Ser Gly Arg Gly Lys Ser Phe Thr Leu Thr Ile Thr
        275                 280                 285

Val Phe Thr Asn Pro Pro Gln Val Ala Thr Tyr His Arg Ala Ile Lys
    290                 295                 300

Val Thr Val Asp Gly Pro Arg Glu Pro Arg Arg His Arg Gln Lys Leu
305                 310                 315                 320

Asp Asp Ser Lys Pro Ser Leu Phe Ser Asp Arg Leu Ser Asp Leu Gly
                325                 330                 335

Arg Ile Pro His Pro Ser Met Arg Val Gly Val Pro Pro Gln Asn Pro
            340                 345                 350

Arg Pro Ser Leu Asn Ser Ala Pro Ser Pro Phe Asn Pro Gln Gly Gln
        355                 360                 365

Ser Gln Ile Thr Asp Pro Arg Gln Ala Gln Ser Ser Pro Pro Trp Ser
    370                 375                 380

Tyr Asp Gln Ser Tyr Pro Ser Tyr Leu Ser Gln Met Thr Ser Pro Ser
385                 390                 395                 400
```

```
Ile His Ser Thr Thr Pro Leu Ser Ser Thr Arg Gly Thr Gly Leu Pro
            405                 410                 415

Ala Ile Thr Asp Val Pro Arg Arg Ile Ser Asp Asp Thr Ala Thr
            420                 425                 430

Ser Asp Phe Cys Leu Trp Pro Ser Ser Leu Ser Lys Lys Ser Gln Ala
            435                 440                 445

Gly Ala Ser Glu Leu Gly Pro Phe Ser Asp Pro Arg Gln Phe Pro Ser
            450                 455                 460

Ile Ser Ser Leu Thr Glu Ser Arg Phe Ser Asn Pro Arg Met His Tyr
465                 470                 475                 480

Pro Ala Thr Phe Thr Tyr Thr Pro Pro Val Thr Ser Gly Met Ser Leu
            485                 490                 495

Gly Met Ser Ala Thr Thr His Tyr His Thr Tyr Leu Pro Pro Pro Tyr
            500                 505                 510

Pro Gly Ser Ser Gln Ser Gln Ser Gly Pro Phe Gln Thr Ser Ser Thr
            515                 520                 525

Pro Tyr Leu Tyr Tyr Gly Thr Ser Ser Ala Ser Tyr Gln Phe Pro Met
            530                 535                 540

Val Pro Gly Gly Asp Arg Ser Pro Ser Arg Met Val Pro Pro Cys Thr
545                 550                 555                 560

Thr Thr Ser Asn Gly Ser Thr Leu Leu Asn Pro Asn Leu Pro Asn Gln
            565                 570                 575

Asn Asp Gly Val Asp Ala Asp Gly Ser His Ser Ser Ser Pro Thr Val
            580                 585                 590

Leu Asn Ser Ser Gly Arg Met Asp Glu Ser Val Trp Arg Pro Tyr
            595                 600                 605

<210> SEQ ID NO 11
<211> LENGTH: 457
<212> TYPE: PRT
<213> ORGANISM: Artificial
<220> FEATURE:
<223> OTHER INFORMATION: LMP-1 HUMAN

<400> SEQUENCE: 11

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
            35                  40                  45

Trp Val Leu Ser Ile Asp Gly Glu Asn Ala Gly Ser Leu Thr His Ile
        50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
            85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
            115                 120                 125

Pro Gln Gln Asn Gly Gln Pro Leu Arg Pro Leu Val Pro Asp Ala Ser
            130                 135                 140

Lys Gln Arg Leu Met Glu Asn Thr Glu Asp Trp Arg Pro Arg Pro Gly
145                 150                 155                 160
```

```
Thr Gly Gln Ser Arg Ser Phe Arg Ile Leu Ala His Leu Thr Gly Thr
            165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
            195                 200                 205

Pro Trp Pro Gly Pro Thr Ala Pro Ser Pro Thr Ser Arg Pro Pro Trp
210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
            245                 250                 255

Ser Arg Thr Ser Ile Val Gln Ala Ala Ala Gly Gly Val Pro Gly Gly
            260                 265                 270

Gly Ser Asn Asn Gly Lys Thr Pro Val Cys His Gln Cys His Lys Val
            275                 280                 285

Ile Arg Gly Arg Tyr Leu Val Ala Leu Gly His Ala Tyr His Pro Glu
            290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
            325                 330                 335

Tyr Ala Pro Ser Cys Ala Lys Cys Lys Lys Ile Thr Gly Glu Ile
            340                 345                 350

Met His Ala Leu Lys Met Thr Trp His Val His Cys Phe Thr Cys Ala
            355                 360                 365

Ala Cys Lys Thr Pro Ile Arg Asn Arg Ala Phe Tyr Met Glu Glu Gly
            370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
            405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
            435                 440                 445

Cys Lys Ser His Ala Phe Ser His Val
450                 455

<210> SEQ ID NO 12
<211> LENGTH: 457
<212> TYPE: PRT
<213> ORGANISM: Artificial
<220> FEATURE:
<223> OTHER INFORMATION: LMP-1 MOUSE

<400> SEQUENCE: 12

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
            35                  40                  45

Trp Val Leu Asn Ile Asp Gly Glu Asn Ala Gly Ser Leu Thr His Ile
50                  55                  60
```

-continued

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Leu Thr
            85                  90                  95

Pro Pro Ala Asp Pro Pro Arg Tyr Thr Phe Ala Pro Ser Ala Ser Leu
            100                 105                 110

Asn Lys Thr Ala Arg Pro Phe Gly Ala Pro Pro Thr Asp Ser Thr
            115                 120                 125

Leu Arg Gln Asn Gly Gln Leu Leu Arg Gln Pro Val Pro Asp Ala Ser
            130                 135                 140

Lys Gln Arg Leu Met Glu Asp Thr Glu Asp Trp Arg Pro Arg Pro Gly
145                 150                 155                 160

Thr Gly Gln Ser Arg Ser Phe Arg Ile Leu Ala His Leu Thr Gly Thr
            165                 170                 175

Glu Phe Met Gln Asp Pro Asp Glu Glu Phe Met Lys Lys Ser Ser Gln
            180                 185                 190

Val Pro Arg Thr Glu Ala Pro Ala Pro Ala Ser Thr Ile Pro Gln Glu
            195                 200                 205

Ser Trp Pro Gly Pro Thr Thr Pro Ser Pro Thr Ser Arg Pro Pro Trp
210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
            245                 250                 255

Asn Arg Thr Ser Ile Val Gln Ala Ala Ala Gly Gly Gly Thr Gly Gly
            260                 265                 270

Gly Ser Asn Asn Gly Lys Thr Pro Val Cys His Gln Cys His Lys Ile
            275                 280                 285

Ile Arg Gly Arg Tyr Leu Val Ala Leu Gly His Ala Tyr His Pro Glu
            290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Ser Cys Tyr Asp Val Arg
            325                 330                 335

Tyr Ala Pro Asn Cys Ala Lys Cys Lys Lys Ile Thr Gly Glu Ile
            340                 345                 350

Met His Ala Leu Lys Met Thr Trp His Val His Cys Phe Thr Cys Ala
            355                 360                 365

Ala Cys Lys Thr Pro Ile Arg Asn Arg Ala Phe Tyr Met Glu Glu Gly
            370                 375                 380

Ala Pro Tyr Cys Glu Arg Asp Tyr Glu Lys Met Phe Gly Thr Lys Cys
385                 390                 395                 400

Arg Gly Cys Asp Phe Lys Ile Asp Ala Gly Asp Arg Phe Leu Glu Ala
            405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Asp Lys Pro Leu
            435                 440                 445

Cys Lys Ser His Ala Phe Ser His Val
450                 455